United States Patent [19]

McDonald et al.

[11] Patent Number: 4,822,812

[45] Date of Patent: Apr. 18, 1989

[54] β-(FLUOROMETHYLENE)-5-HYDROXY-TRYPTOPHAN AND DERIVATIVES AND THEIR USE AS PRODRUGS FOR MAO INHIBITION

[75] Inventors: Ian A. McDonald, Loveland; Michael G. Palfreyman, Cincinnati, both of Ohio; Jean-Noël Collard, Bischheim, France

[73] Assignee: Merrell Dow Pharmaceuticals Inc., Cincinnati, Ohio

[21] Appl. No.: 53,212

[22] Filed: May 21, 1987

[51] Int. Cl.$^4$ .................. A61K 31/405; C07D 209/20
[52] U.S. Cl. ..................................... 514/419; 548/496
[58] Field of Search ......................... 548/496; 514/419

[56] References Cited

U.S. PATENT DOCUMENTS

| | | | |
|---|---|---|---|
| 4,029,807 | 7/1977 | Roldau et al. | 548/496 |
| 4,421,767 | 12/1983 | Palfreyman | 424/319 |
| 4,454,158 | 6/1984 | Beg | 424/330 |

OTHER PUBLICATIONS

Bioorg. Chem. 14, 103 (1986) Ian A. McDonald et al.

*Primary Examiner*—David B. Springer
*Attorney, Agent, or Firm*—Louis J. Wille

[57] ABSTRACT

This invention relates to pharmacologically-active novel compounds comprising β-fluoromethylene-5-hydroxytryptophan and derivatives, to methods of inhibiting monoamine oxidase and to treating depression, and to pharmaceutical compositions containing the compounds.

14 Claims, No Drawings

β-(FLUOROMETHYLENE)-5-HYDROXYTRYPTOPHAN AND DERIVATIVES AND THEIR USE AS PRODRUGS FOR MAO INHIBITION

This invention relates to pharmacologically-active novel compounds, to methods of inhibiting monoamine oxidase and to treating patients suffering from depression, and to pharmaceutical compositions containing the compounds.

The class of compounds known as monoamine oxidase inhibitors (MAO inhibitors) has been employed in psychiatry for over 20 years for the treatment of depression. MAO inhibitors currently used in the U.S.A. for treating depression include tranylcypromine, phenelzine and isocarboxazid. MAO inhibitors can also be employed to treat other psychiatric disorders, such as phobic anxiety states. In addition, another MAO inhibitor, pargyline is available for the treatment of hypertension.

It is believed that the MAO inhibitors act to alleviate psychiatric disorders, such as depression, by increasing the concentration of one or more biogenic monoamines in the central nervous system. The monoamine oxidase enzyme (MAO) plays an important role in the metabolic regulation of the monoamines since it catalyzes the biodegradation of the monoamines through oxidative deamination. By inhibiting MAO, the degradation of the monoamines is blocked and the result is an increase in the availability of the monoamines for their physiological functions. Among the physiologically active monoamines which are known substrates for MAO are: (a) so-called "neurotransmitter" monoamines, such as the catecholamines (e.g., norepinephrine, dopamine) and 5-hydroxytryptamine, (b) the so-called "trace" amines (e.g., tryptamine, o-tyramine, phenethylamine, tele-N-methylhistamine), and (c) tyramine.

The usefulness of the MAO inhibitors in treating depression has been limited because the administration of such agents can potentiate the pharmacological action of certain food substances or drugs leading to dangerous and sometimes lethal effects. For example, persons receiving a MAO inhibitor must avoid the ingestion of foods which have a high tyramine content (such as cheese) because the MAO inhibitor will block the metabolic degradation of tyramine in the gut and liver resulting in high circulating levels of tyramine, consequent release of catecholamines in the periphery, and finally serious hypertension. The potentiation by a MAO inhibitor of the pressor effect of tyramine arising from the ingestion of cheese, and the hypertensive episode produced thereby, are commonly known as the "cheese reaction" or "cheese effect". Moreover, persons on conventional MAO therapy can not be given directly-acting sympathomimetic drugs (or precursors thereof) which are themselves substrates for MAO (e.g., dopamine, epinephrine, norepinephrine, or L-dopa) or indirectly-acting sympathomimetic drugs (e.g. amphetamines or over-the-counter cold, hay-fever, or weight control preparation which contain a vasoconstrictor). The potentiation of the pressor effects of indirectly-acting sympathomimetic drugs is especially profound. This is because such drugs act peripherally primarily by releasing catecholamines in nerve endings, and the concentration of the liberated cathecholamines will be dangerously elevated if the metabolic degradation of the catecholamines via MAO is blocked.

In one aspect, the present invention encompasses compounds of the formula (I):

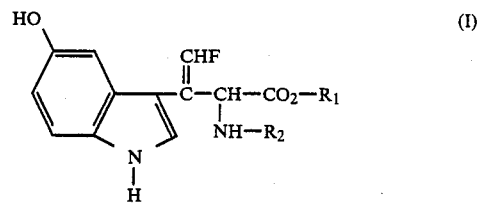

wherein $R_1$ is hydrogen or a lower alkyl group and $R_2$ is hydrogen or a formyl group; or a non-toxic pharmaceutically acceptable salt thereof.

The term "lower alkyl group" contemplates alkyl radicals consisting of 1 to 4 carbon atoms of straight or branced-chain configuration and includes methyl, ethyl, propyl, isopropyl, butyl, sec-butyl, and t-butyl. The term "formyl group" contemplates a radical of the formula HCO-.

In compounds of formula (I), hydrogen, methyl and ethyl are preferred for substituent $R_1$ and hydrogen is preferred for substituent $R_2$.

Suitable non-toxic pharmaceutically acceptable salts of the compounds of formula (I) are well known in the art and include acid addition salts formed by protonation of an amino group and salts formed by neutralization of a carboxylic acid function. When the compounds of formula (I) are in the form of an amino acid, such compounds may exist as a zwitterion. Examples of acid addition salts are those formed from the following acids: hydrochloric, hydrobromic, sulfonic, sulfuric, phosphoric, nitric, maleic, fumaric, benzoic, ascorbic, pamoic, succinic, methanesulfonic, acetic, propionic, tartaric, citric, lactic, malic, mandelic, cinnamic, palmitic, itaconic, and benzenesulfonic. Examples of salts formed by neutralization of the carboxylic acid are metallic salts (e.g., sodium, potassium, lithium, calcium, or magnesium) and ammonium or (substituted) ammonium salts. The potassium and sodium salts are preferred.

The compounds of formula (I) are in vivo precursors (or "prodrugs") of certain substances which are irreversible inhibitors of MAO, and said compounds are useful in psychiatry for the treatment of patients suffering from depression. The compounds of formula (I) are not irreversible inhibitors of MAO in vitro. In order to produce irreversible inhibitors of MAO in vivo and to exert their antidepressant effect, the compounds of formula (I) must be transformed into a novel active metabolite which is the β-fluoromethylene-5-hydroxytryptamine shown below as formula (II).

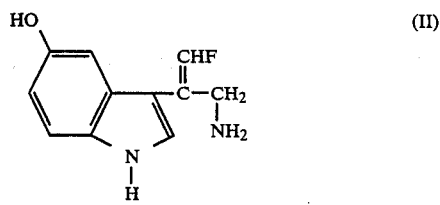

The in vivo transformation of the compounds of formula (I), to the active metabolite of formula (II) occurs through a decarboxylation reaction catalyzed by an enzyme known as "aromatic L-amino acid decarboxylase" (AADC). AADC is known to decarboxylate various biologically important amino acids (such as L-dopa, m-tyrosine, phenylalanine, tryptophan, and 5-hydroxytryptophan) to form the corresponding monoamines. When compounds of formula (I) are in the form of an ester of the carboxylic acid or formyl-substituted amine, such compounds are not substrates for AADC. Hence, before decarboxylation can take place, the ester or amide functions are hydrolyzed in vivo, either enzymatically or non-enzymatically, to provide a compound of formula (I) wherein $R_1$ and $R_2$ are hydrogen.

Because AADC exists in the brain and in extracerebral tissues, the decarboxylation of a compound of formula (I) to form the corresponding metabolite of formula (II) will occur both cerebrally and extracerebrally. The amount of compound available extracerebrally for brain penetration can be increased by administering the compound of formula (I) in combination with a compound capable of preferentially inhibiting extracerebral AADC. Thus, when administered in combination with an extracerebral AADC inhibitor, the compounds of formula (I) will provide a "site-directed" or "site-selective" inhibition of MAO, such inhibition occurring preferentially in the brain rather than in extracerebral tissues.

As compared to the administration of a compound of formula (I) alone, the administration of a compound of formula (I) in combination with an extracerebral AADC inhibitor may achieve a pharmacologically meaningful beneficial effect on brain MAO activity using less administered compound. Moreover, this effect may be obtained with proportionally less propensity for producing the "cheese effect" or other peripheral complications associated with extracerebral MAO inhibition.

Suitable AADC inhibitors for use in combination with the compounds of formula (I) will be apparent to those skilled in the art. Both competitive and irreversible inhibitors can be used. At the dosages used, the AADC inhibitor must be capable of substantially inhibiting AADC extracerebrally without substantially inhibiting AADC in the brain. Examples of AADC inhibitors for use in combination with a compound of formula (I) are carbidopa and benserazide, compounds which also have been found useful for blocking the peripheral decarboxylation of exogenous L-dopa administered for the treatment of Parkinsonism. Other examples of suitable AADC inhibitors are the 2-amino-2-(mono or di-fluoromethyl)-3-(mono or dihydroxyphenyl)propionic acids and like compounds, which are described in Belgian Pat. Nos. 868,881 and 882,105. Preferred compounds are carbidopa and benserazide.

Compounds of formula (I) can be prepared as outlined in Reaction Scheme A:

REACTION SCHEME A

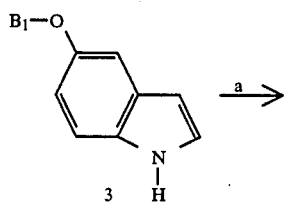

-continued
REACTION SCHEME A

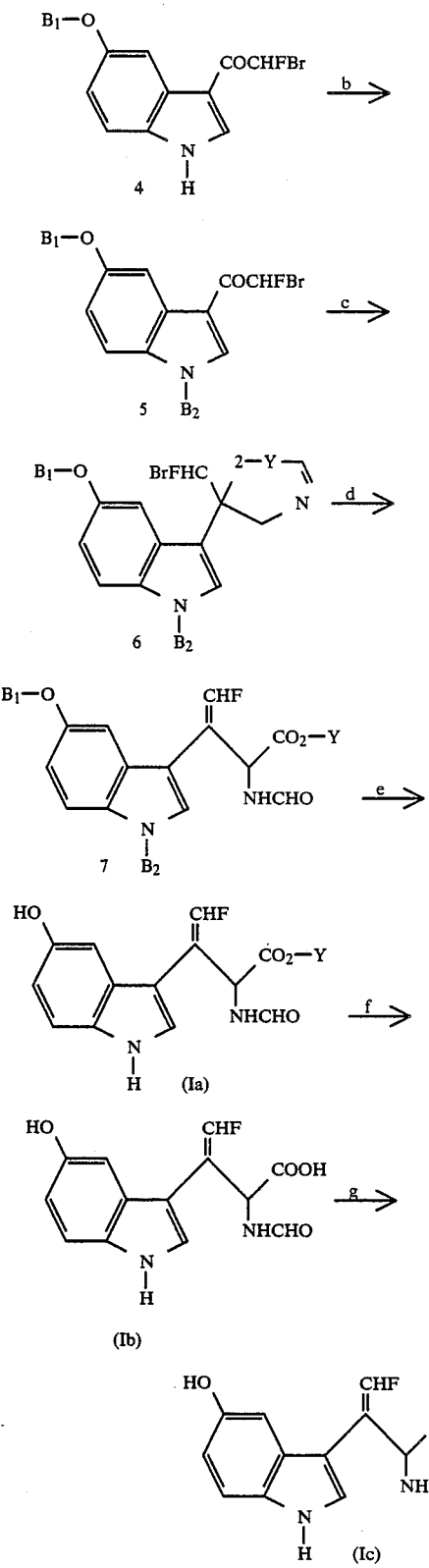

wherein $B_1$ is a protecting group for an aromatic hydroxy group, $B_2$ is a protecting group for a heterocyclic amine, and Y is a lower alkyl group as previously defined. The groups represented by $B_1$ and $B_2$ are any groups known to be useful in the art of chemistry for protecting an aromatic hydroxy group and a heterocyclic amino group, respectively, during the synthesis described below and which are readily removable under conditions which will not cause side reactions (such as polymerization) involving the double bond. Examples of suitable protecting groups making up $B_1$ are $C_1$–$C_6$ alkyl, tetrahydropyranyl, methoxymethyl, methoxyethoxy-methyl, t-butyl, benzyl, and triphenylmethyl. The term $C_1$–$C_6$ alkyl refers to a saturated hydrocarbyl radical of one to six carbon atoms of straight, branched, or cyclic configuration. Preferred protecting groups are those that can be removed under very mild conditions. Methyl is most preferred for $B_1$. Examples of suitable protecting groups making up $B_2$ are p-toluenesulfonyl (tosyl), benzenesulfonyl, benzyloxycarbonyl, (substituted)-benzyloxycarbonyl (e.g., the p-chloro, p-bromo, p-nitro, p-methoxy, p-chloro, 2,4-dichloro, and 2,6-dichloro derivatives), t-butyloxycarbonyl (Boc), t-amyloxycarbonyl, isopropyloxycarbonyl, 2-(p-biphenyl)-isopropyloxycarbonyl, allyloxycarbonyl, cyclopentyloxycarbonyl, cyclohexyloxycarbonyl, and adamentyloxycarbonyl. The preferred heterocyclic amino protecting group is t-butyloxycarbonyl (Boc) which can be introduced by reaction with di-t-butyl dicarbonate. The selection and utilization of particular blocking groups represented by $B_1$ and $B_2$ are well known in the art of chemistry. Ethyl is preferred for Y.

In step (a) starting material 3, such as 5-methoxyindole, is condensed with bromofluoroacetyl chloride according to the procedure described by Bergman (J. Heterocyclic Chem., 7, 1071 (1970)). The bromofluoroacetyl chloride is prepared by the procedure described by Middleton (J. Org. Chem., 44, 2291 (1979)).

The 5-substituted 3-bromofluoroacetylindole (4) thus formed is further reacted in step (b) with an appropriate blocking agent to obtain 5 in which the heterocyclic amino group is protected. The Boc derivative is preferred for 5 and is obtained by reacting 4 with di-t-butyl dicarbonate in the presence of catalytic amounts of p-dimethylaminopyridine (DMAP) as described by Grehn and Ragnarsson (Angew. Chem. Int. Ed. Engl., 23, 296 (1984)).

The oxazolines (6) are obtained by reacting 5 with an appropriate ester of isocyanoacetic acid in step (c) by essentially the method of Heinzer and Bellus (Helv. Chim. Acta, 64, 2279 (1981)). The isocyanoacetate should be selected to provide the desired ester of the carboxylic acid. Ethyl isocyanoacetate is preferred. Since these oxazolines (6) are moderately unstable, the preferred method of purifying 6 comprises evaporating the reaction mixture of step (c) to dryness, redissolving 6 in diethyl ether in which 5 remains essentially insoluble, and passing the ether solution through celite.

A reductive elimination of 6 is then effected to yield a mixture of the Z and E isomers of the β-(fluoromethylenetryptophan derivative (7) in step (d). It is preferred to carry out the reduction by reacting 6 with zinc after pre-treatment of 6 with trifluoroacetic acid (TFA) or a mixture of TFA and trifluoroacetic anhydride in a ratio of about 20:1 respectively. A mixture of Z and E isomers of the β-(fluoromethylene)tryptophan derivatives are isolated from by-products also formed in step (d) by chromatography on silica gel after silylating the byproducts by treating the reaction product of step (d) with bis-(trimethylsilyl)-acetamide (BSA).

The protecting groups ($B_1$ and $B_2$) present in the (E/Z)-β-(fluoromethylene)tryptophan derivatives are removed in step (e) to yield the ester of (E/Z)-N-formyl β-(fluoromethylene)-5-hydroxytryptophan (Ia). Conditions under which various protecting groups are removed from an aromatic alcohol and a heterocyclic amine can be used. These conditions for the various protecting groups are well known in the art of chemistry. It is preferred to remove the protecting groups by conditions under which minimal degradation of reactant or product occurs. Where $B_1$ is methyl and $B_2$ is Boc, the preferred method for step (e) is to react 7 with $BBr_3$ followed by water hydrolysis.

The ester is converted to the carboxylic acid in step (f) by hydrolysis of the ester using a base reactive enough to hydrolyze the ester and yet mild enough to prevent excessive degradation of the reactant or product. The preferred base to effect hydrolysis of the (E)-configured isomer is lithium hydroxide at a molar concentration of about twice that of the ester and at about room temperature. Under these conditions, however, the (Z)-configured isomer of (Ia) decomposes. By careful optimization of the reaction conditions (such as the base used, reaction temperature, reaction time, solvent) in a manner known in the art of chemistry, the Z-configured isomer of (Ib) can be prepared.

The compounds of the formula (Ib) are converted to (E/Z)-β-(fluoromethylene)-5-hydroxytryptophan (Ic) in step (g) by treating (Ib) with a protic acid and then with propylene oxide. It is preferred to use hydrochloric acid at about 2N final concentration and to carry out the reaction at room temperature. The (E/Z)-β-(fluoromethylene)-5-hydroxytryptophan (Ic) thus formed is further reacted to form various esters, α-N-substituted derivatives, and 5-hydroxy-substituted derivatives in reactions well known in the art.

In addition, compounds of the formula (I) can be synthesized from 5-methoxy-3-acetylindole by a method incorporating a Wittig-type reaction in a manner analogous to that described by McDonald et al. (Bioorg. Chem. 14, 103 (1986)). This approach will result in the virtually exclusive synthesis of the (E)-configured isomer of compounds of the formula (I).

It will be appreciated by those skilled in the art that the compounds of formula (I) can bear substituents, as are well known and appreciated in the art, which are capable of being removed in vivo, either enzymatically or non-enzymatically, to generate compounds of formula (I) in vivo. For example, the aromatic hydroxy moiety of compounds of the formula (I) can be derivatized to an ester of a lower alkyl carboxylic acid; the amino moiety of compounds of formula (I) can be derivatized to amides of lower alkyl carboxylic acids; the carboxylic acid moiety of compounds of formula (I) can be derivatized to an amide involving an amino group or a lower alkyl substituted amino group. It will also be appreciated by those skilled in the art that these derivatives of compounds of formula (I) which contain such substituents at the aromatic hydroxy, the carboxylic acid, or the amino groups, can also be utilized to inhibit MAO in vivo and to treat depressed patients. Therefore such derivatives are the equivalents of compounds of the formula (I) for the purposes of this invention.

Since the compounds of formula (I) possess an asymmetric carbon atom, enantiomers are possible, and the compounds of the invention may be in the form of an individual enantiomer or mixtures of the enantiomers, such as the racemate.

The compounds of formula (I) may be obtained in the form of a pure enantiomer either by resolving a desired racemic product or by resolving a racemic intermediate at any convenient stage of the synthesis. Methods of carrying out the resolution are well known in the art of chemistry. When dosage ranges are given herein, they are applicable to the racemate.

In addition, the compounds of formula (I) can exist in forms wherein the fluorine substituent can be either cis or trans to the indole group. It is understood that the compounds of the invention may exist as the pure cis or pure trans form, or as mixtures thereof.

The compounds of formula (II) can be made enzymatically by contacting the compound of formula (Ic) with AADC under standard conditions well known in the art. In addition, the compound of formula (II) can be made chemically by a method analogous to that disclosed in U.S. Pat. No. 4,454,158.

Compounds of formula (I) can be used in treating patients suffering from depression or in inhibiting MAO in the brain of a patient in need thereof by administration of an effective dose. An effective dose is one which produces the desired pharmacological effect in improving the clinical symptoms of depression or in inhibiting MAO in the brain. An effective dose can vary according to the particular compound being employed, the severity and nature of the disease, and the particular subject being treated. In general, effective results can be achieved by the oral or parenteral route at a dosage level of from about 20 to about 200 mg per day. Therapy should be initiated at lower dosages, the dosage thereafter being increased until the desired effect is achieved.

When compounds of formula (I) are administered in combination with an effective dose of an AADC inhibitor the minimum effective dose for compounds of formula (I) will typically be lower than the minimum effective dose in the absence of co-administration of an AADC inhibitor.

The effective dosage of the AADC inhibitor must be capable of substantially blocking the AADC catalyzed decarboxylation of said compound extracerebrally without substantially blocking the AADC catalyzed decarboxylation in the brain. The effective dose will vary, however, according to the particular compound being employed and the dose of the antidepressant "prodrug" administered. In general, with carbidopa and benserazide, effective results can be achieved by the oral or parenteral route at a dosage level of about 50 to 500 mg per day, preferably about 50 to 250 mg. With the 2-halomethylated 2-amino-3-(substituted phenyl)-propionic acids described above, effective results can be achieved by the oral or parenteral route at a dosage level of about 0.1 mg to 1000 mg per day. For example, with 2-amino-2-difluoromethyl-3-(3',4'-dihydroxyphenyl)propionic acid, and like compounds, the effective dose is about 10 to 1000 mg per day, preferably about 100 to 500 mg. With 2-amino-2-fluoromethyl-3-(3',4'-dihydroxyphenyl)propionic acid, and like compounds, such as the 2,3-dihydroxyphenyl isomer thereof, the effective dose is about 0.1 to 50 mg per day, preferably about 0.5 to 10 mg.

It will be understood that the AADC inhibitor can be co-administered either substantially at the same time as, or prior to, the administration of a compound of formula (I). When administered prior to a compound of formula (I), the AADC inhibitor can be given up to 4 hours before the compound of formula (I). The exact dosage schedule will depend upon the route of administration and severity of the condition being treated.

When used in combination with an AADC inhibitor, a compound of formula (I) and the AADC inhibitor can be administered separately, each being contained in a formulation in which the compound or the AADC inhibitor is the sole active agent, or they can be administered together in a formulation containing both the compound and the AADC inhibitor as active agents. When both agents are contained in a single formulation, the relative amounts of each agent can vary depending upon the particular compounds employed.

The compounds of this invention can be administered in various manners to achieve the desired effect. The compounds can be administered alone or in combination with pharmaceutically acceptable carriers or excipients, the proportion and nature of which are determined by the solubility and chemical properties of the compound selected, the chosen route of administration, and standard pharmaceutical practice. The compounds may be administered orally in solid dosage forms, e.g., capsules, tablets, powders, or in liquid forms, e.g., solutions or suspensions. The compound may also be injected parenterally in the form of sterile solutions or suspensions. Solid oral forms may contain conventional excipients, for instance: lactose, sucrose, magnesium stearate, resins, and like materials. Liquid oral forms may contain various flavoring, coloring, preserving, stabilizing, solubilizing, or suspending agents. Parenteral preparations are sterile aqueous or nonaqueous solutions or suspensions which may contain various preserving, stabilizing, buffering, solubilizing, or suspending agents. If desired, additives, such as saline or glucose, may be added to make the solutions isotonic.

The amount of active compound administered will vary and can be any effective amount. Unit doses of these compounds can contain, for example, from about 10 μg to 100 mg of the compounds and may be administered, for example, one or more times daily, as needed.

The term "unit dosage form" is used herein to mean a single or multiple dose form containing a quantity of the active ingredient in admixture or otherwise in association with pharmaceutically acceptable carriers or excipients, said quantity being such that one or more predetermined units are normally required for a single therapeutic administration.

In another embodiment of the invention pharmaceutical compositions comprising an effective amount of a compound of the formula (I) in combination with a pharmaceutically acceptable carrier or excipient are provided.

Pharmaceutical compositions comprising an effective amount of a compound of formula (I) and an effective amount of an aromatic L-amino acid decarboxylase inhibitor in admixture with pharmaceutically acceptable carriers or excipients thereof are also contemplated as being within the scope of the invention. Preferred AADC inhibitors are benserazide, carbidopa, and a 2-amino-3-(mono- or dihydroxyphenyl)propionic acid.

The pharmaceutical compositions are prepared in a manner well known per se in the pharmaceutical art. The carrier or excipient may be solid, semi-solid, or liquid material which can serve as a vehicle or medium for the active ingredient. Suitable carriers or excipients are well known in the art per se. The pharmaceutical composition may be adapted for enteral or parenteral use and may be administered to the patient in the form of tablets, capsules, suppositories, solution, suspensions, or the like.

In order to more fully illustrate the preparation of the compounds of this invention, the following examples are provided. The examples are illustrative only and are not intended to limit the scope of the invention in any way.

EXAMPLE 1

3-Bromofluoroacetyl-5-methoxyindole

Add bromofluoroacetyl chloride (7.42 grams (g), 42.3 millimoles (mmole)) dropwise to a well-stirred solution of 5-methoxyindole (6.22 g, 42.3 mmol) and pyridine (3.4 milliliters (ml), 42.3 mmol) in dioxan (50 ml) at 0° C. After addition, remove the cooling bath and stir the mixture for 1 hour (h). Pour the mixture into water (150 ml) and stir for 0.5 h. Filter the resulting mixture and recrystallize the resulting crude product from ethanol yielding 3-bromofluoroacetyl-5-methoxyindole (8.1 g, 67% yield); m.p.=184°–185° C.; NMR (acetone-$d_6$) $\delta$3.87 (s, 3H), 6.80–7.03 (m, 2H), 7.03 (d, J=50 Hz, 1H), 7.45 (d, J=8 Hz, 1H), 7.87 (d, J=2 Hz, 1H), 8.27–8.40 (m, 1H), 11.07 (broad s, 1H).

EXAMPLE 2

1-(t-Butyloxycarbonyl)-3-bromofluorocetyl-5-methoxyindole

To a well stirred solution of 3-bromofluoroacetyl-5-methoxyindole (7.5 g, 26.22 mmol) and 4-dimethylaminopyridine (0.24 g, 2.62 mmol) in 150 ml of tetrahydrofuran (THF) add dropwise di-t-butyl dicarbonate (6.3 g, 28.9 mmol) at room temperature and allow to react for 1 h. Evaporate the THF and the t-butanol from the resulting mixture and stir the crude product in diethyl ether for 1 h. Collect the product by filtration and recrystallize in acetone to yield 1-(t-butyloxycarbonyl)-3-bromofluoroacetyl-5-methoxyindole; (9.11 g, 90% yield); mp 165°–166° C., NMR (acetone-$d_6$) $\delta$1.70 (s, 9H), 3.85 (s, 3H), 6.83–7.13 (m, 1H), 7.01 (d, J=50 Hz, 1H), 7.63–8.17 (m, 2H), 8.47–8.63 (m, 1H).

EXAMPLE 3

4-Ethylcarboxylate-5-bromofluoromethyl-5-(5-methoxy-1-t-butyloxycarbonylindole)-2-oxazoline Add ethyl isocyanoacetate (2.64 g, 23.32 mmole) and $Cu_2O$ (150 mg) to a solution of 1-(t-butyloxycarbonyl)-3-bromofluoroacetyl-5-methoxyindole (9 g, 23.32 mmole) in 300 ml of THF and stir at room temperature for 18 h. Remove the THF, add 200 ml of diethyl ether and stir for 0.5 h. Filter the mixture and pass the filtrate through a celite column to remove the copper salts. Remove the diethyl ether to yield 4-ethylcarboxylate-5-bromofluoromethyl-5-(5-methoxy-1-t-butyloxycarbonyl)indole)-2-oxazoline (8.2 g, 70.5% yield) as a pasty solid, 3 isomers (2E-1Z: 52–48), NMR (CDCL$_3$) $\delta$0.80 and 0.83 (2t, J=7 Hz, 3H of E isomers), 1.37 (t, J=7 Hz, 3H of Z isomer), 1.63 (s, 9H), 3.37–3.97 (m, 2H of E isomers), 3.82 (s, 3H), 4.34 (q, J=2 Hz, 2H of Z isomer), 5.05–5.30 (m, 1H), 5.95–8.17 (m, 7H).

EXAMPLE 4

Ethyl 2-Formylamino-3-(5-methoxy-1-t-butyloxycarbonylindole)-4-fluoro-3-butenoate To a solution of 4-ethylcarboxylate-5-bromofluoromethyl-5-(5-methoxy-1-t-butyloxycarbonyl)indole-2-oxazoline (2.77 g, 5.55 mmole) in 50 ml of N,N-dimethyl formamide at 0° C. add dropwise trifluoroacetic acid (0.43 ml, 5.57 mmole). After 15 minutes add zinc wool (1.09 g, 16.6 mmole) and stir at room temperature for 24 h. Filter the mixture and pour the filtrate into 200 ml of water. Extract the (E/Z) isomers of ethyl 2-formylamino-3-(2-t-butyloxycarbonylindole)-4-fluoro-3-butenoate into 200 ml of diethyl ether. Remove the diethyl ether after washing with water. Separate the (Z) configured stereoisomer by chromatography on silica by eluting with 40% petroleum ether in diethyl ether (0.115 g, 4.9% yield). Separate the (E) configured isomer from hydrolysis products of the oxazolines which elute with it by removing the solvent, redissolving the product in 20 ml of $CH_3CN$, refluxing the solution for 1 h in the presence of bis-(trimethylsilyl)-acetamide (0.47 g, 2.31 mmole), removing the solvent, and re-chromatographing under the same conditions as above (0.33 g, 13.9% yield). Total yield 18.8% (Z/E=26/74). Z isomer (yellow oil), NMR (CDCl$_3$) $\delta$1.27 (t, J=7 Hz, 3H), 1.63 (s, 9H), 3.77 (s, 3H), 4.17 (q, J=7 Hz, 2H), 5.77 (d, J=8 Hz, 1H), 6.47–7.07 (m, 3H), 6.87 (d, J=82 Hz, 1H), 7.50 (s, 1H), 7.97 (d, J=9 Hz, 1H), 8.13 (s, 1H). E isomer (yellow oil, NMR (CDCl$_3$) $\delta$1.20 (t, J=7 Hz, 3H), 1.63 (s, 9H), 3.77 (s, 3H), 4.15 (q, J=7 Hz, 2H), 5.33 (d, J=8 Hz 1H), 6.57–7.03 (m, 3H), 7.42 (s, 1H), 7.73 (d, J=80 Hz, 1H), 7.91 (d, J=9 Hz, 1H), 8.12 (s, 1H).

EXAMPLE 5

Ethyl 2-Formylamino-3-(5-methoxy-1-t-butyloxycarbonylindole)-4-fluoro-3-butenoate Use the same procedure as described in Example 4 except treat the oxazolines (8.2 g, 16.43 mmole) with a mixture of trifluoroacetic acid (1.27 ml, 16.43 mmole) and trifluoroacetic anhydride (0.12 ml, 0.85 mmol) to yield the Z configured isomer (0.35 g, 5% yield) and the E configured isomer (1.03 g, 14.5% yield). Total yield 19.5% (Z/E=26/74).

EXAMPLE 6

(E)-Ethyl 2-Formylamino-3-(5-hydroxyindole)-4-fluoro-3-butenoate

To a stirred solution 0.35 g (0.83 mmole) of (E)-ethyl 2-formylamino-3-(5-methoxy-1-t-butyloxycarbonylindole)-4-fluoro-3-butenoate in 15 ml $CH_2Cl_2$ add 2.5 mmoles of $BBr_3$ (molar in $CH_2Cl_2$) while maintaining the mixture at 0° C. Allow the mixture to come to room temperature and continue stirring for 1 h. Add 4 ml of water and continue stirring for 1 h. Neutralize the mixture with the addition of a saturated solution of sodium bicarbonate and extract the crude product continuously with $CH_2Cl_2$ for 24 h. Purify by chromatography on silica gel eluting with 10% ethanol in $CHCl_3$ yielding (E)-ethyl 2-formylamino-3-(5-hydroxyindole)-4-fluoro-3-butenoate (0.15 g, 59% yield). NMR (CD$_3$OD) $\delta$1.15 (t, J=7 Hz, 3H), 4.10 (q, J=7 Hz, 2H), 5.77 (s, 1H), 6.53–7.30 (m, 4H), 6.85 (d, J=84 Hz, 1H), 7.97 (s, 1H).

EXAMPLE 7

(Z)-Ethyl 2-Formylamino-3-(5-hydroxyindole)-4-fluoro-3-butenoate

Use the same procedure as described in Example 6 to convert 0.6 g (1.43 mmole) (Z)-ethyl 2-formylamino-3-(5-methoxy-1-t-butyloxycarbonylindole)-4-fluoro-3-butenoate to 0.37 g (Z)-ethyl 2-formylamino-3-(5-hydroxyindold)-4-fluoro-3-butenoate in 85% yield. NMR (CD$_3$O) δ1.13 (t, J=7 Hz, 3H), 4.08 (q, J=7 Hz, 2H), 5.27 (broad s, 1H), 6.50–7.23 (m, 4H), 6.92 (d, J=82 Hz, 1H), 7.97 (s, 1H).

EXAMPLE 8

(E)-Fluoromethylene-5-hydroxytryptophan

Treat a solution of 0.35 g (1.1 mmole) (E)-ethyl 2-formylamino-3-(5-hydroxyindole)-4-fluoro-3-butenoate in 4 ml of dimethoxyethane (DME) and 1 ml of water with 53 milligrams (2.2 mmole) of LiOH for 2 h at room temperature under nitrogen. Remove the DME, add 10 ml of water, and wash the solution 2 times with 10 ml CH$_2$Cl$_2$ each time. Add 10 ml of 4 N HCl to the aqueous solution and stir for 24 h at room temperature under N$_2$. Filter and lyophilize the resulting solid product (free acid). Dissolve the product in 10 ml of isopropanol, treat with charcoal, filter, and treat with 0.23 ml (3.3 mmole) of propylene oxide for 24 h at room temperature under nitrogen. Collect the resulting crystals by filtration under nitrogen, wash with diethyl ether, and dry to yield 65 mg of (E)-β-fluoromethylene-5-hydroxytryptophan in 22% yield. mp>250° C., $^1$H NMR 360 MHz (D$_2$O)δ4.54 (s, 1H), 6.86–6.98 (9 m, 2H), 7.20 (d, J=81.4 Hz, 1H), 7.30 (s, 1H), 7.42 (d, J=8.7 Hz, 1H) $^{19}$F NMR 338.84 MHz (D$_2$O), CF$_3$CO$_2$H external ref. δ42.68 (dd, J=81.0 Hz and 3.0 Hz).

We claim:

1. A compound of the formula (I):

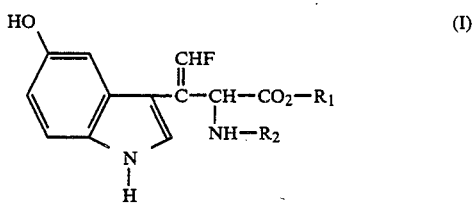

wherein R$_1$ is hydrogen or a lower alkyl group and R$_2$ is hydrogen or a formyl group; or a non-toxic pharmaceutically acceptable salt thereof.

2. A compound as defined in claim 1 wherein the fluorine substituent is situated cis with respect to the indole moiety.

3. A compound as defined in claim 1 wherein the fluorine substituent is situated trans with respect to the indole moiety.

4. A mixture of isomers as described in claim 1 wherein the fluorine substituent is situated cis and trans with respect to the indole moiety.

5. A compound as defined in claim 1 wherein R$_1$ and R$_2$ are each hydrogen.

6. A compound as defined in claim 1 wherein R$_1$ is ethyl and R$_2$ is formyl.

7. Compounds as defined in claims 5 or 6 wherein the fluorine substituent is situated cis with respect to the indole moiety.

8. Compounds as defined in claims 5 or 6 wherein the fluorine substituent is situated trans with respect to the indole moiety.

9. A mixture of isomers as described in claims 5 or 6 wherein the fluorine substituent is situated cis and trans with respect to the indole moiety.

10. A composition comprising (a) a compound as defined in claim 1, and (b) a pharmaceutically acceptable carrier or excipient.

11. A composition as defined in claim 10 in unit dosage form containing 10 μg to 100 mg of said compound per unit dose.

12. A method for treating patients suffering from depressiion which comprises administering to said patient an effective amount of a compound as defined in claim 1.

13. A method for inhibiting monoamine oxidase in the brain which comprises administering to a patient in need thereof an effective amount of a compound as defined in claim 1.

14. A method as defined in claim 13 wherein said compound is (E)-β-fluoromethylene-5-hydroxy-tryptophan.

* * * * *